United States Patent [19]

Saville

[11] Plant 5,045

[45] May 3, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 307,378

[22] Filed: Oct. 1, 1981

[51] Int. Cl.[3] ..... A01H 5/00

[52] U.S. Cl. ..... Plt./9

[58] Field of Search ..... Plt./9

*Primary Examiner*—Robert E. Bagwill
*Attorney, Agent, or Firm*—Vincent G. Gioia

[57] ABSTRACT

A new miniature rose variety of Jasper red flower coloring with slightly lighter colored petal edges borne singly and in large sprays.

1 Drawing Figure

The present invention relates to a new and distinct variety of rose plant of the miniature rose class, which was originated by my crossing as seed parent the rose known as "Sheri Anne" (U.S. Plant Pat. No. 3,826) and the rose known as "Watercolor" (U.S. Plant Pat. No. 4,031) as pollen parent.

Among the novel characteristics possessed by this new variety which distinguish it from its parents and all other varieties of which I am aware are flowers of unusual Jasper red coloring borne singly and in large sprays. Flowers are Jasper red with lighter colored petal edges and darker toned petal undersurface with distinct lighter toned veining. The flower's unique coloring is delightfully displayed against attractive glossy green foliage. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Color Chart (RHSCC). The terminology used in color description herein refers to plate numbers in the aforementioned color chart, e.g., "39A" is plate 39A of The Royal Horticultural Society Color Chart.

Parentage: Seedling.
*Seed parent.*—"Sheri Anne".
*Pollen parent.*—"Watercolor".
Class: Miniature The following observations are made of specimens grown outdoors in Essex County, Mass. during the month of July.

FLOWER

Blooming habit: Continuous, recurrent

A. Bud:
(1) *Size.*—Medium.
(2) *Form.*—Short pointed, ovate.
(3) *Color.*—When sepals first divide — 39A. When petals begin to unfurl the lighter colored top petal surfaces edges 39C is first seen.

(4) *Sepals.*—Simple, straight, slightly longer than bud with pale grey fuzzy edge.
(5) *Penduncle.*—Length — 1 to 1¼ inches. Aspect — straight, strong. Strength — erect. Color — brownish green.

B. Bloom:
(1) *Size.*—Average size when fully expanded — about 1¼ to 1½ inches.
(2) *Borne.*—Singly and in sprays of 3 to 10 blooms.
(3) Form.—High centered at first opening flat, petals reflex and quill to points.
(4) *Petalage.*—Number of petals under normal conditions — about 35 to 40.
(5) *Color.*—As buds open and petals unfurl predominant Jasper red coloring 39A to 39B is most apparent. Petal undersurface is darker toned 39A with distinct veining 39C. Also seen is some light colored petal streaking on the undersurface which may be very light pink to white. Darker tones 39A appear where petals bunch and lighter colors such as 48D at petal edges.

C. Petals:
(1) *Texture.*—Thick, heavy substance.
(2) *Appearance.*—Top satiny, undersurface matte.
(3) *Form.*—Wide oval with short point at tip.
(4) *Arrangement.*—Regular.
(5) *Petaloids in center.*—Few.
(6) *Persistence.*—Slow to drop.
(7) *Fragrance.*—Slight.
(8) *Lasting quality.*—Long lasting on plant and as cut flower.

REPRODUCTIVE ORGANS

A. Stamens, filaments and anthers:
(1) *Arrangement.*—Stamens regular, arranged around styles.
(2) *Color.*—16A.

B. Pollen:
*Color.*—17B.

C. Styles: Bunched, uneven length.

D. Stigmas:
*Color.*—55C.

E. Hips:
*Shape.*—Globular.
*Size.*—Medium.
*Color.*—Orange (mature).
Do seeds protrude?—No.

PLANT

A. Form: Upright.

B. Growth: Very vigorous.

*Height attained.*—About 14 to 18 inches.

C. Foliage: Compound 5 to 7 leaflets.

(1) *Size.*—Medium to large for miniature.

(2) *Quantity.*—Abundant.

(3) *Color.*—Foliage: Upper side — near 139A. Under side — near 137B.

(4) *Shape.*—Oval.

(5) *Texture.*—Upper side is glossy and under side is flat.

(6) *Edge.*—Serrate tending to double serrate.

(7) *Serration.*—Significant.

(8) *Leaf stem.*—Color — green with reddish cast.

(9) *Stipules.*—Medium, slightly bearded.

(10) *Resistance to disease.*—Blackspot — better than average. Mildew — better than average.

D. Wood:

(1) *New wood.*—Color — near 146B to C. Bark — smooth.

(2) *Old wood.*—Color — near 143A. Bark — smooth.

E. Thorns:

(1) *Thorns.*—Quantity (main stalk): few. On laterals from stalk — ordinary. Form — long pointed, curved slightly downward. Length — medium. Color — near 183A. Position — irregular.

(2) Prickles.—None.

F. Winter hardiness: Good winter hardiness.

I claim:

1. A new and distinct variety of rose plant of the miniature class, substantially as shown and described, characterized particularly by attractive Jasper red flowers borne singly and in large sprays.

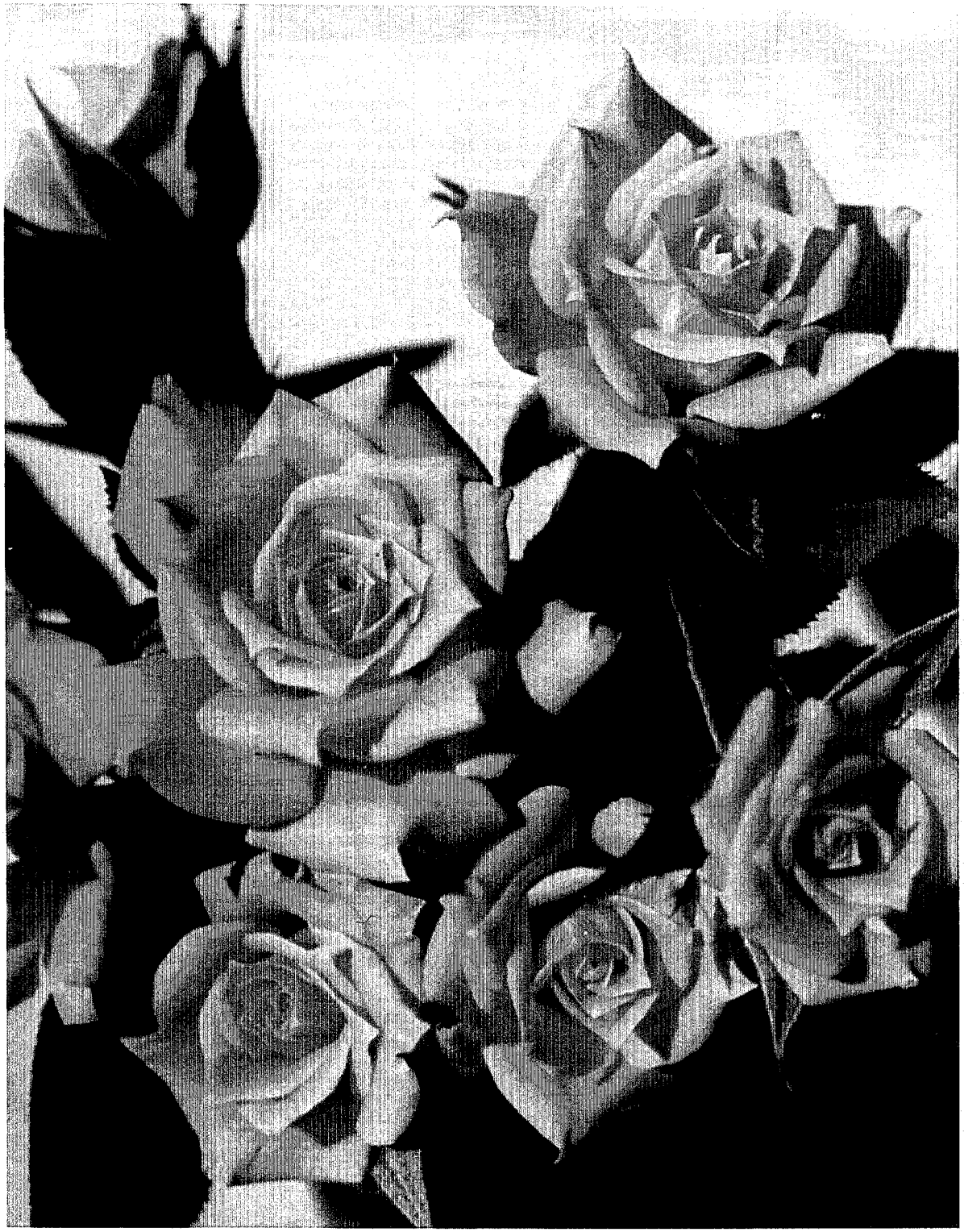

* * * * *